(12) United States Patent
McKinney

(10) Patent No.: US 8,618,522 B2
(45) Date of Patent: Dec. 31, 2013

(54) FLOW THROUGH APPARATUS FOR UV DISINFECTION OF WATER

(76) Inventor: Jerry L. McKinney, Silsbee, TX (US)

( * ) Notice: Subject to any disclaimer, the term of this patent is extended or adjusted under 35 U.S.C. 154(b) by 0 days.

(21) Appl. No.: 13/189,116

(22) Filed: Jul. 22, 2011

(65) Prior Publication Data

US 2013/0020500 A1  Jan. 24, 2013

(51) Int. Cl.
*C02F 1/32* (2006.01)

(52) U.S. Cl.
USPC .................................. 250/504 R; 210/748.1

(58) Field of Classification Search
USPC .......... 250/504 R, 431, 432 R, 434, 435, 436; 210/748.1, 748.11, 748.12, 748.14, 210/194, 224, 256, 257.1, 261, 262, 321.72, 210/321.73, 748.15; 362/217.16, 217.17
See application file for complete search history.

(56) References Cited

U.S. PATENT DOCUMENTS

| | | | | |
|---|---|---|---|---|
| 3,637,342 A | * | 1/1972 | Veloz | 250/436 |
| 3,767,918 A | * | 10/1973 | Graybeal | 250/433 |
| 3,971,338 A | * | 7/1976 | Alexson | 119/262 |
| 4,253,949 A | * | 3/1981 | Hines et al. | 210/703 |
| 4,780,200 A | * | 10/1988 | Bond et al. | 210/194 |
| 5,019,256 A | | 5/1991 | Ifill et al. | |
| 5,256,299 A | | 10/1993 | Wang et al. | |
| 5,422,487 A | | 6/1995 | Sauska et al. | |
| 5,527,453 A | * | 6/1996 | Hachima | 210/150 |
| 5,624,573 A | | 4/1997 | Wiesmann | |
| 5,709,799 A | * | 1/1998 | Engelhard | 210/748.1 |
| 5,753,106 A | * | 5/1998 | Schenck | 210/96.1 |
| 5,843,309 A | * | 12/1998 | Mancil | 210/205 |
| 6,296,775 B1 | | 10/2001 | Moody et al. | |
| 6,638,420 B2 | * | 10/2003 | Tyllila | 210/86 |
| 6,691,781 B2 | * | 2/2004 | Grant et al. | 166/265 |
| 6,932,912 B2 | * | 8/2005 | Chaffin | 210/754 |
| 7,025,889 B2 | * | 4/2006 | Brodie | 210/748.11 |
| 7,081,225 B1 | * | 7/2006 | Hollander | 210/748.11 |
| 7,250,610 B1 | | 7/2007 | Cox et al. | |
| 7,279,092 B2 | | 10/2007 | Moody et al. | |
| 7,727,406 B2 | * | 6/2010 | Lam | 210/764 |
| 2002/0162969 A1 | * | 11/2002 | Reed | 250/432 R |
| 2004/0134861 A1 | * | 7/2004 | Brodie | 210/748 |
| 2005/0115880 A1 | * | 6/2005 | Pollock | 210/194 |
| 2005/0211639 A1 | * | 9/2005 | Nguyen et al. | 210/748 |
| 2006/0124860 A1 | * | 6/2006 | Shim | 250/432 R |
| 2006/0163168 A1 | | 7/2006 | Moody et al. | |

* cited by examiner

*Primary Examiner* — Phillip A Johnston
*Assistant Examiner* — Brooke Purinton
(74) *Attorney, Agent, or Firm* — Bushman & Associates, P.C.

(57) ABSTRACT

A system for disinfecting contaminated water having, in one embodiment, a vessel for contaminated water having an inlet and an outlet. An elongate housing is disposed generally vertically in the vessel, the housing having a housing inlet and a housing outlet, the housing outlet being in open communication with the interior of the vessel. An elongate UV light assembly is disposed in the housing and divides at least a portion of the housing into first and second flow pathways, the second flow pathway being in open communication with the housing outlet. There is a flow inducer aiding flow of at least some of the contaminated water from the vessel, through the housing and out the housing outlet.

18 Claims, 8 Drawing Sheets

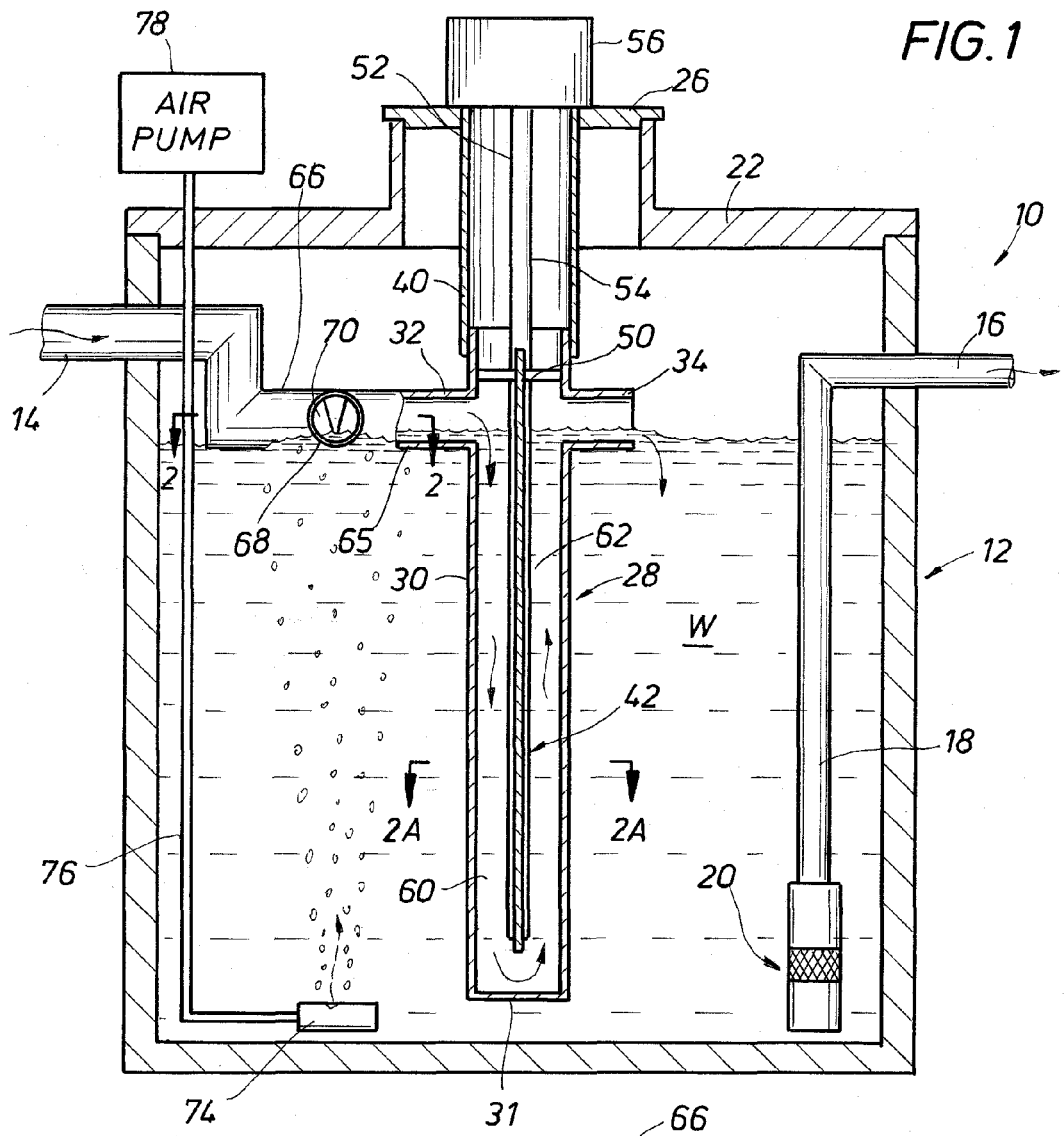
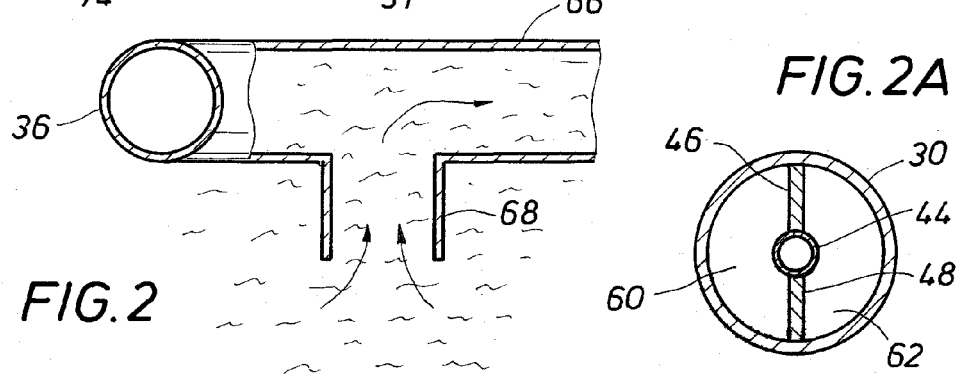

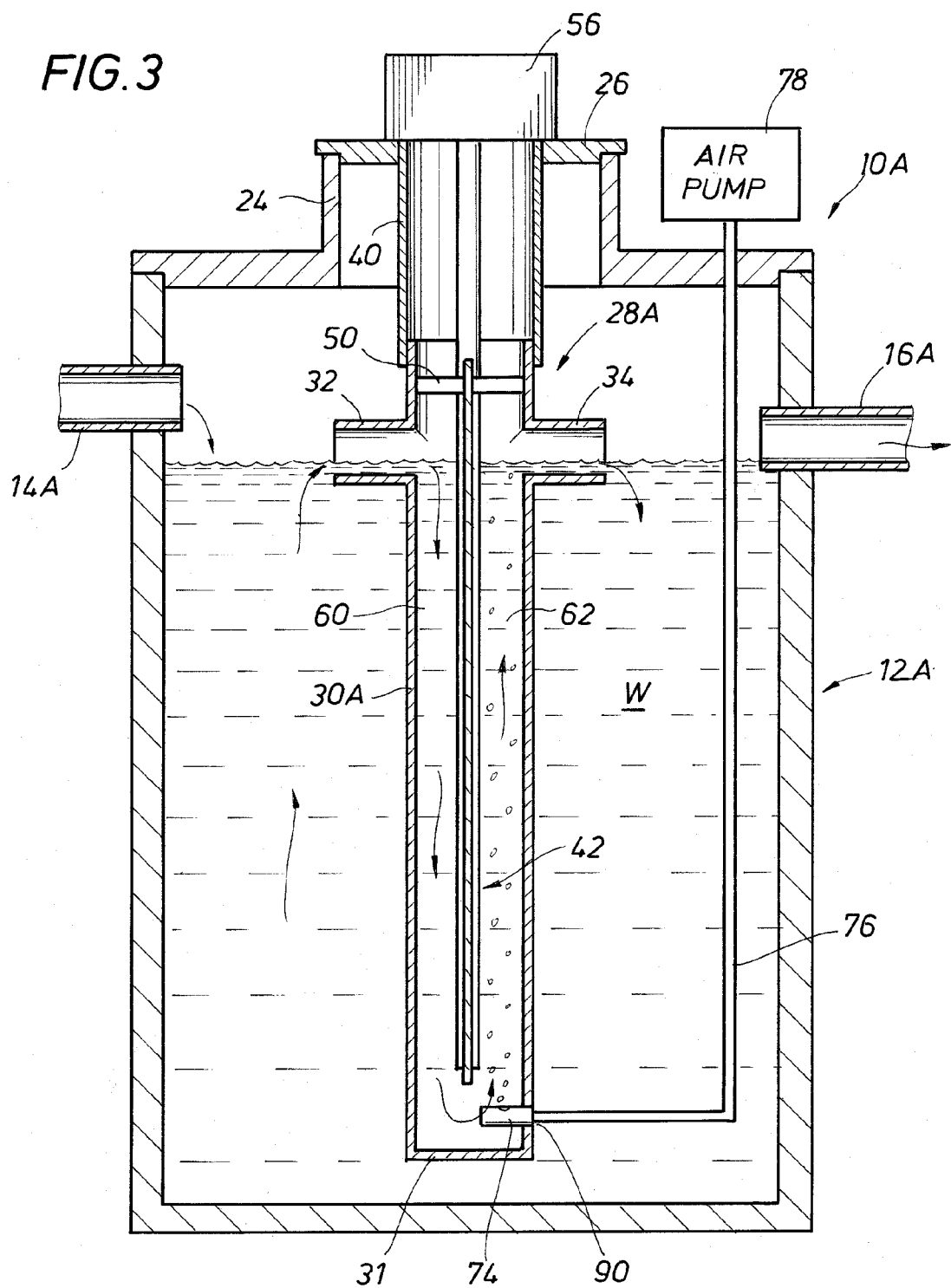

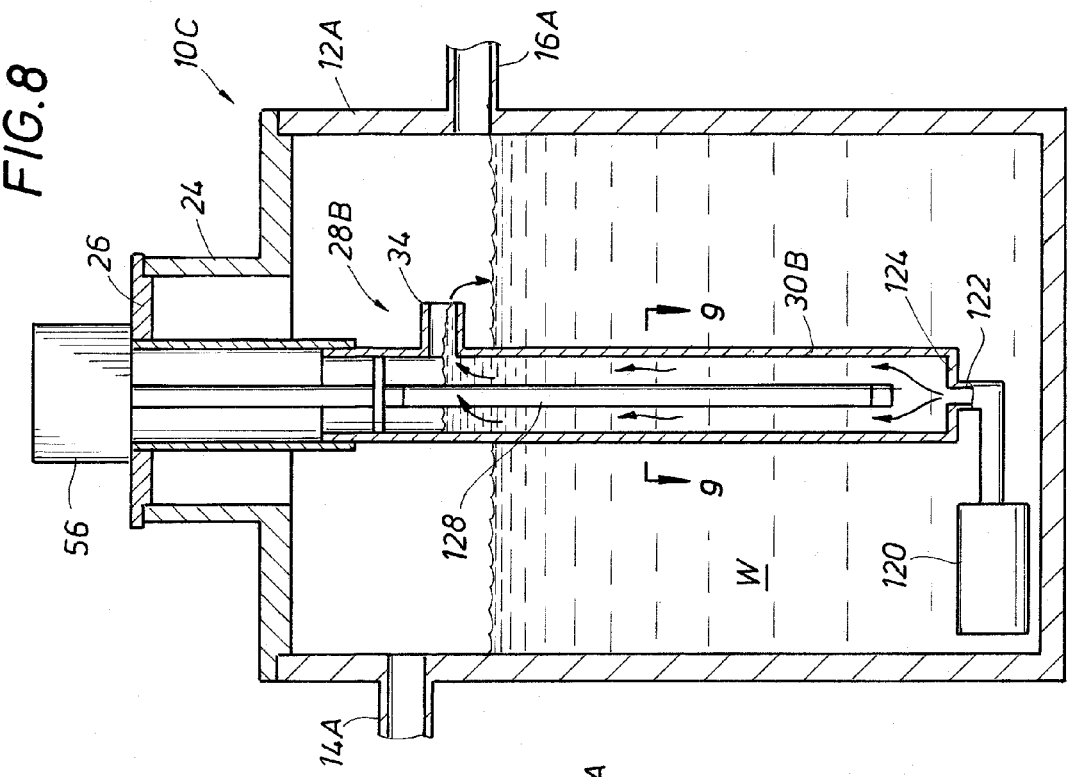
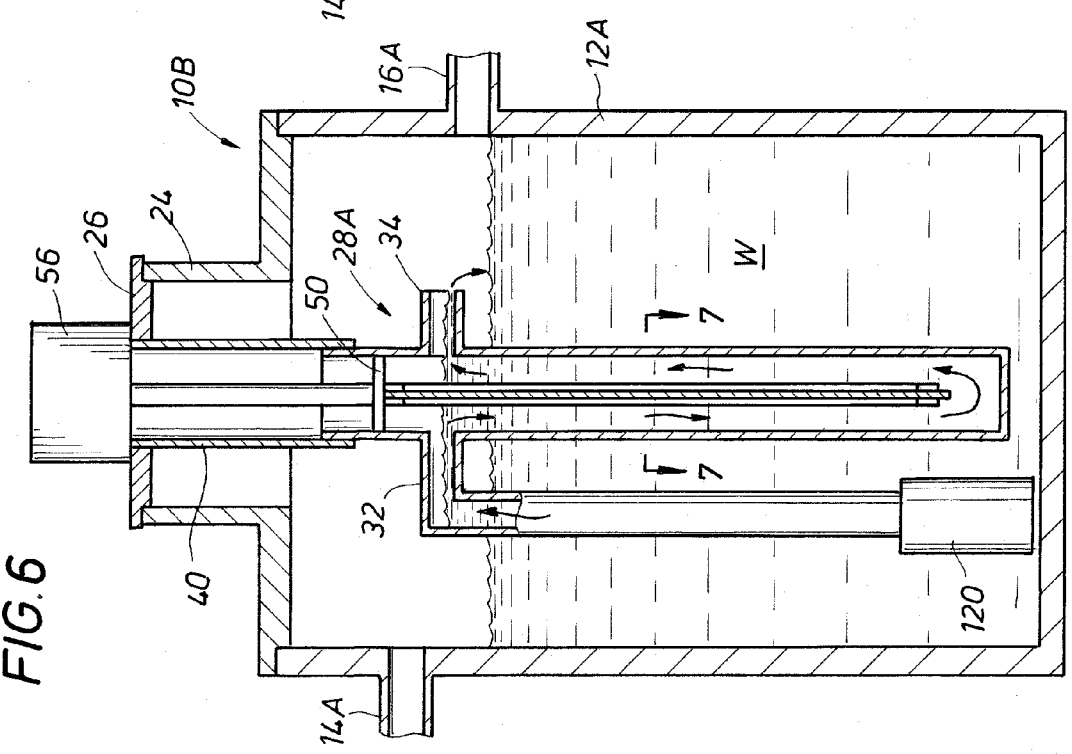

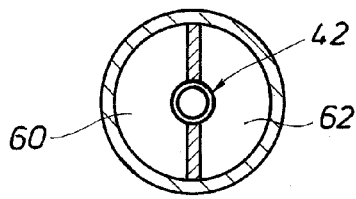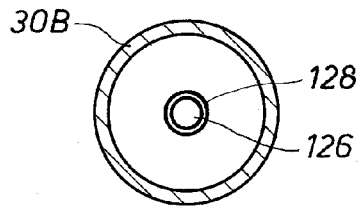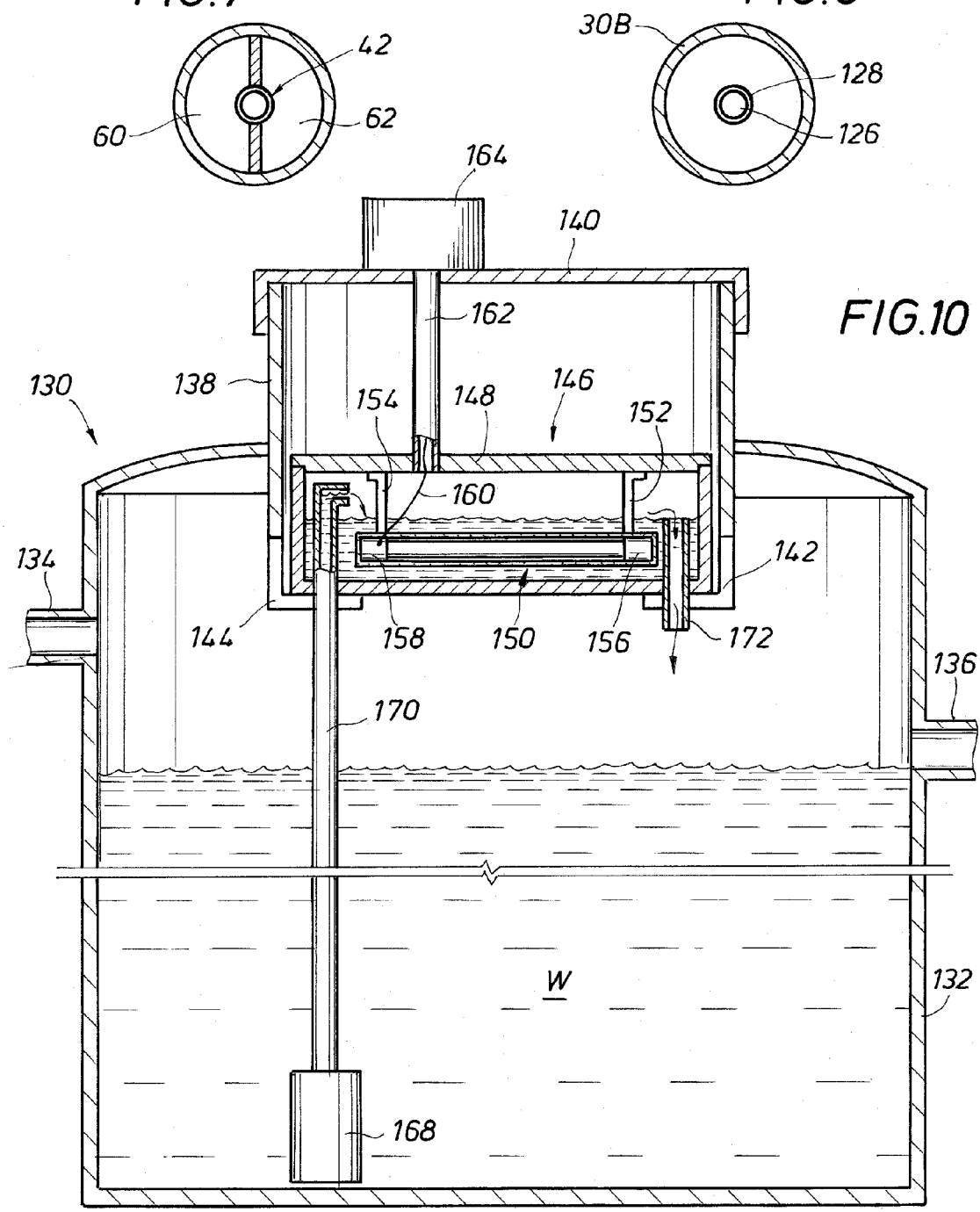

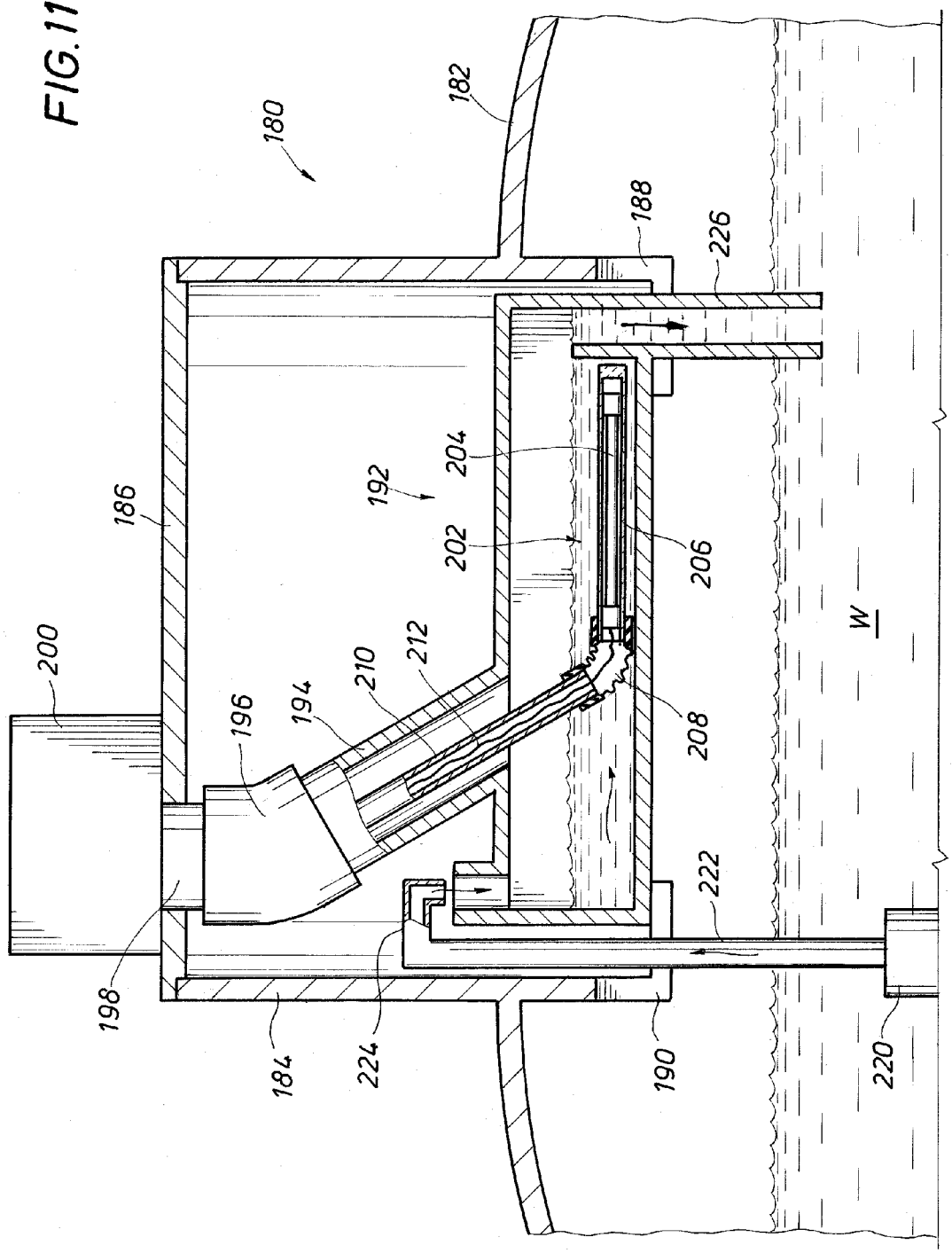

FLOW THROUGH APPARATUS FOR UV DISINFECTION OF WATER

FIELD OF THE INVENTION

The present invention relates to disinfecting contaminated water and, more specifically, disinfecting contaminated water using ultraviolet radiation.

BACKGROUND OF THE INVENTION

Many homes and small businesses, particularly in rural and outlying areas which are not connected to rural treatment systems rely on septic tank systems, aerobic treatment systems, small package plants or other types of local treatment apparatus (collectively "packaged plants") for wastewater treatment. These packaged plants generally use one or more tanks containing the treatment apparatus connected to a field drip system or drain field for ultimate disposal of the treated waters. Treatment entails degradation of waste in the water by the biological processes of bacteria and microorganisms. This "treated wastewater" generally contains bacteria and other microorganisms.

The fluid quality produced by packaged plants is usually regulated by one or more governmental agencies, most of which require that the discharged wastewater be disinfected to reduce the potential hazards caused by the bacteria/microbes in the treated effluent. One common type of disinfection treatment is chemical treatment with a chlorine type compound. Another common treatment is radiation with ultraviolet light (UV). What is known in the radiation of water with UV within the range from about 150 nm through about 300 nm is effective in destroying microorganisms. See for example U.S. Pat. Nos. 5,019,256; 5,256,299; 5,422,487; or 5,624,573. Prior art UV treatment systems are shown, for example, in U.S. Pat. Nos. 6,296,775, 7,250,610, 7,279,092, as well as U.S. Publication 2006/0163168, all of which are incorporated herein by reference for all purposes.

In addition to treated wastewater there also exists a problem in disinfecting contaminated water from other sources. In many areas of the world infrastructure which provides potable water for human use, e.g., consumption, baths, etc. is inadequate. For example, in many parts of the world while municipal water may be delivered to residential or commercial sites, the pumping systems do not produce sufficient water pressure to service all of the household needs of the numerous residences attached or connected to the municipal system. This may also be true of a single, large well serving multiple dwellings. In many instances, it is common to place a holding tank on the elevated portion of the residence, e.g., the roof, pump the water into the holding tank, and then use the head pressure of the water at the elevated location to accommodate normal household needs such as showers, faucets, etc. Still another problem with municipal water in these somewhat underdeveloped locations is that the water may become contaminated due to inadequate chlorination, leaking pipes, etc. Accordingly, even though the water is from a municipal system, it is still contaminated and can cause serious illness. Lastly, since the water in these environments is in the holding tanks as described above and may be quiescent for undesirable periods of time, at elevated temperatures there is a chance for the growth of microorganisms, bacteria and the like which would again contaminate the water prior to use.

SUMMARY OF THE INVENTION

In one aspect the present invention provides a UV disinfection system for contaminated water wherein the contaminated water is more efficiently and effectively disinfected prior to discharge.

In another aspect the present invention provides a UV disinfection system for contaminated water which is readily accessible for maintenance.

Still another aspect of the present invention provides a US disinfection system in combination with an alternative energy source.

These and further features and advantages of the present invention will become apparent from the following detailed description, wherein reference is made to the figures in the accompanying drawings.

BRIEF DESCRIPTION OF THE DRAWINGS

FIG. 1 is a side, elevational view, partly in cross-section, of one embodiment of the UV disinfection system of the present invention.

FIG. 2 is cross-sectional view taken along the line 2-2 of FIG. 1.

FIG. 2A is a cross-sectional view taken along the lines 2A-2A of FIG. 1.

FIG. 3 is a view similar to FIG. 1 showing another embodiment of the disinfecting system of the present invention.

FIG. 6 is a view similar to FIG. 1 showing another embodiment of the disinfecting system of the present invention.

FIG. 7 is a view similar to FIG. 1 showing another embodiment of the disinfecting system of the present invention. FIG. 7 is a cross-sectional view taken along the lines 7-7 of FIG. 6.

FIG. 8 is a view similar to FIG. 1 of another embodiment of the disinfecting system of the present invention.

FIG. 9 is a cross-sectional view taken along the lines 9-9 of FIG. 8.

FIG. 10 is an elevational view, partly in section, of another embodiment of the disinfecting system of the present invention.

FIG. 11 is a partial elevational view, partly in section, showing another embodiment of the disinfecting system of the present invention.

DETAILED DESCRIPTION OF PREFERRED EMBODIMENTS

Figure 4:
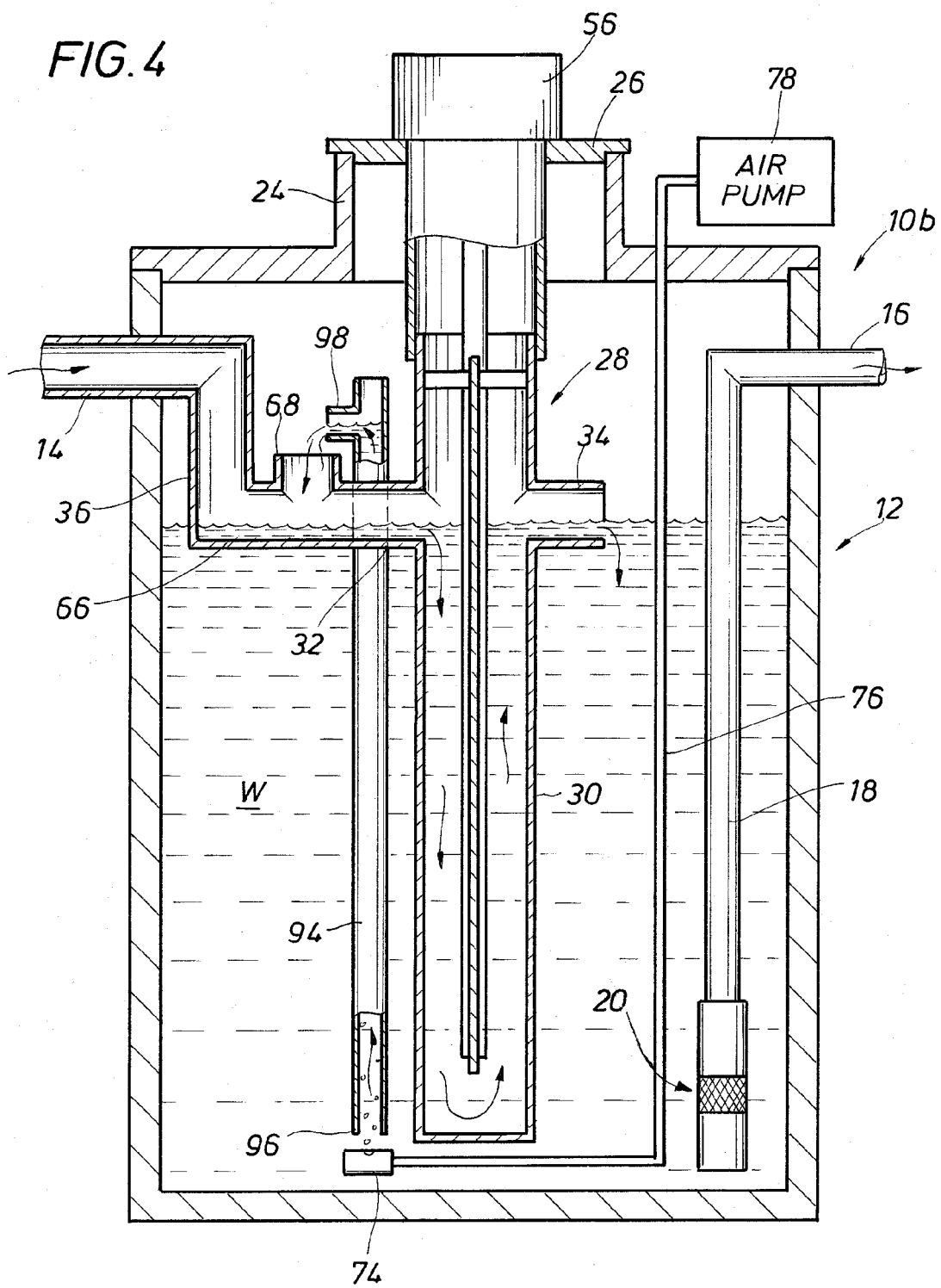
FIG. 4 is a view similar to FIG. 1 showing still another embodiment of the disinfecting system of the present invention.

As used herein, the term "treated wastewater" generally refers to wastewater from a septic system which has been subjected to a pretreatment or settling tank to remove large solids and aerobic digestion to produce substantially clarified, treated wastewater. The term "contaminated water" refers to treated wastewater as well as water from other sources which is intended to be used as potable water or at the very least relatively bacteria and microorganism free water. Thus, in the description which follows, treated wastewater and contaminated water may be used inter-changeably.

Referring to FIG. 1 the disinfectant system shown generally as 10 comprises a pump vessel 12 having a volume W of treated wastewater therein. Pump vessel 12 has an inlet 14 and an outlet 16, inlet 14 being connected to a source of clarified treated wastewater from a packaged plant, outlet 16 being connected by riser pipe 18 to a pump 20 for pumping wastewater W out of outlet 16 from vessel 12. Vessel 12 has a cover 22 with a neck portion 24 and an access hatch 26 which can be removed and the interior of pump vessel 12 accessed for maintenance or the like.

Disposed in pump vessel 12 is a UV disinfecting unit shown generally as 28. UV unit 28 comprises a substantially elongate housing 30 generally vertically mounted in pump vessel 12 and extending into treated wastewater W in vessel 12. As seen, housing 30 has an inlet 32 and an outlet 34, inlet 32 being connected by a T-fitting 65 to a conduit 36 to inlet 14 to vessel 12, outlet 34 being in open communication with the interior of vessel 12.

Housing 30 is held by a support 40 suspended below hatch 26. Disposed in housing 30 is a UV bulb assembly shown generally as 42, assembly 42 comprising an elongate UV bulb 44 and a frame comprised of partitions 46 and 48, assembly 42 being suspended from a support frame 50 having a suitable seal, gasket, etc. for preventing treated wastewater from entering the space above support frame 50. As seen, UV bulb assembly 42 has a lower end spaced from bottom wall 31 of housing 30. Electrical power wires 52 and 54 are connected to an electrical junction box 56 containing indicators, alarm contacts and other components well known to those skilled in the art. Partitions 46 and 48 shown in FIG. 2A serve to divide the interior of housing 30 into a first flow pathway 60 and a second flow pathway 62. Bulb 44 and partitions 46 and 48 are disposed relative to one another whereby bulb 44 is disposed generally between partitions 46 and 48 such that both the first and second flow pathways are exposed to UV radiation from UV bulb 44. Although not shown, it will be appreciated that UV bulb 44 will be provided with a sleeve above the UV transparent material so as to allow the treated wastewater to be exposed to UV radiation but maintain the bulb out of direct contact with the treated wastewater. As noted, assembly 42 is spaced from the bottom wall 31 of housing 30 whereby flow pathways 60 and 62 are in open communication near the bottom end of housing 30.

T-fitting 65 has a first leg 66 and a second leg 68. First leg 66 is connected on one end to conduit 36 and on the other end to inlet 32 of housing 30. T-fitting 65 is horizontally disposed in vessel 12 such that legs 66 and 68 of T-fitting 65 lie in a generally horizontal plane. Leg 68 is open to the interior of vessel 12 and has disposed therein a weir 70 which can be fixed or adjustable to control the flow of treated wastewater passing into T-fitting 65 and ultimately into inlet 32 of housing 30. It will be appreciated that the T-fitting 65 could be oriented such that leg 68 extended generally downwardly, e.g., in a vertical disposition.

Disposed in the lower end of vessel 12 is a gas dispenser 74 connected to a gas line 76 which in turn is connected to an air pump 78 or other source of gas under pressure.

In operation, as treated wastewater enters inlet 14 of vessel 12 through conduit 36, T-fitting 65, and inlet 32 into housing 30, the treated wastewater flows down pathway 60 around the lower end of the UV bulb assembly 42 and up flow pathway 62 eventually passing into the interior of vessel 12 through outlet 34 of housing 30. As will be appreciated, as the treated wastewater passes down first flow pathway 60 and up second flow pathway 62 it is subjected to radiation from UV bulb 44 in both pathways which disinfects the treated wastewater making it suitable for discharge. The disinfected, treated wastewater is ultimately pumped out of vessel 12 using pump 20 through outlet 16 of vessel 12.

To induce and/or aid flow of treated wastewater through housing 30, gas dispenser 74 is disposed generally vertically below inlet 68 of T-fitting 65. Accordingly, with pump 78 turned on and gas being pumped through gas dispenser 74, the rising bubbles as they move to the surface result in a mounding or raising of a water column such that the level of the treated wastewater W in vessel 12 is now high enough to pass through weir 70 and into inlet 32 of housing 30. So long as air pump 78 is activated, the mounding of water and the inflow through weir 70 and the inlet 32 will continue. As indicated by the arrows, treated wastewater entering inlet 32 of housing 30 passes downwardly through flow pathway 60 and upwardly through flow pathway 62 emptying through outlet 34 back into the water W in vessel 12. Thus, the treated wastewater W in vessel 12 is continuously, so long as pump 78 is actuated, being recycled past UV bulb 44 meaning it is being repeatedly subjected to the UV radiation which ensures a greater disinfecting action. Accordingly, the treated wastewater W from vessel 12 when it is finally discharged via pump 20 and outlet 16, rather than being subjected to a single pass through the UV disinfection unit 28, is subjected to multiple passes.

Turning now to FIG. 3 there is shown another embodiment of the present invention. The system 10A comprises a vessel 12A having an inlet 14A which opens into the interior of vessel 12A and then outlet 16A which permits gravity flow of treated wastewater W out of vessel 12A. Disposed in vessel 12A in a manner similar to that shown in FIG. 1 is a UV disinfecting unit 28A. Disinfecting unit 28A comprises a housing 30A having an opening 90 through which extends a gas line 76 connected to gas dispenser 74. As can be seen, gas dispenser 74 is disposed below second flow pathway 62. The embodiment shown in FIG. 3, unlike that shown in FIG. 1 relies on gravity flow of treated wastewater W out of vessel 12A.

In operation, the system of FIG. 3 works as follows: treated wastewater from a packaged plant enters vessel 12A via inlet 14A. Because the level of outlet 16A is above both the inlet 32 and outlet 34 of housing 30, the treated wastewater W in vessel 12A fills housing 30A and maintains it in that condition. In order to subject treated wastewater W to repeated irradiation from the UV bulb 44, air escaping from dispenser 74 rises upwardly through second flow pathway 62 inducing treated wastewater to flow into housing 30A via inlet 32 and out housing 30A via outlet 34. So long as the pump 78 is running, the recycle or recirculation of treated wastewater W in vessel 12A will continue meaning that it will be subjected to repeated irradiation. Again, this enhances the effectiveness of the killing of bacteria and microbes.

Turning now to FIG. 4, there is shown still another embodiment of the present invention. In the embodiment shown in FIG. 4, treated wastewater from the packaged plant enters vessel 12 via inlet 14 and passes via conduit 36 through T-fitting 65 having legs 66 and 68 as discussed above except that T-fitting 65 is oriented such that legs 66 and 68 lie in a vertical plane, such that the open end of leg 68 is pointing generally upwardly. The embodiment shown in FIG. 4 employs a gas lift assembly to aid the recycle of treated wastewater W through UV disinfection unit 28. In this regard, a tube 94 having an open end 96 extends generally vertically into vessel 12 into treated wastewater W. Tube 94 has a branch 98 which is positioned over the mouth of leg 68 of the T-fitting 65. Disposed below the open end 96 of tube 94 is gas dispenser 74. With pump 78 activated, gas moving up tube 94 carries treated wastewater W in vessel 12 upwardly out branch 98 and into the open mouth of leg 68 of the T-fitting 65. Accordingly, as treated wastewater entering vessel 12 flows into chamber 30, it also carries with it existing treated wastewater W from vessel 12. As long as pump 78 is activated, treated wastewater W in vessel 12 will continuously be lifted by the gas bubbles from gas dispenser 74 into the open end of leg 68, ultimately into and through housing 30. Since outlet 34 is in open communication with the interior of vessel 12, the treated wastewater W in vessel 12 will be repeatedly subjected to UV irradiation, meaning more effective disinfection.

Figure 5:
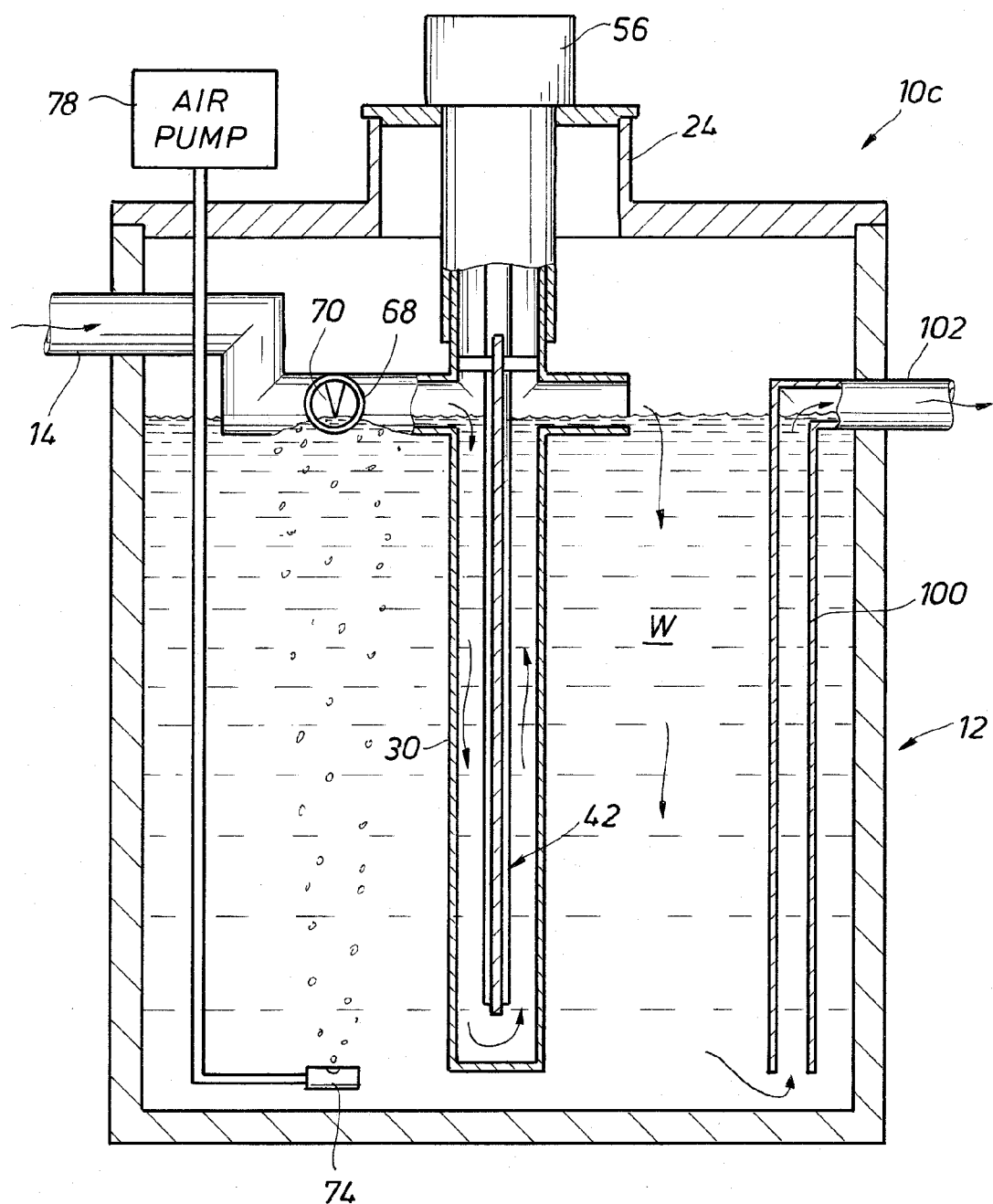
FIG. 5 is a view similar to FIG. 1 showing yet another embodiment of the disinfecting system of the present invention.

Turning now to FIG. 5, there is shown yet another embodiment of the present invention. The embodiment shown in FIG. 5 is substantially that shown in FIG. 1 with the exception that flow of vessel 12 is via gravity as opposed to being pumped out as is the embodiment shown in FIG. 1. In all other respects, the embodiment shown in FIG. 5 operates like the embodiment shown in FIG. 1. Thus, treated wastewater W from vessel 12 which has been repeatedly subjected to UV radiation flows, by gravity, out of stand pipe 100 and outlet 102.

In the embodiments described above, the housing and the UV light assembly disposed therein are positioned in a pump or a holding tank containing treated wastewater. It will be appreciated that the housing containing the UV light assembly could be mounted exterior of the vessel containing the treated wastewater and an external, preferably low volume, pump or the like could be used to take treated wastewater from the holding tank, pass it through the housing containing the UV light assembly and return it to the pump tank which would accomplish the same result of ensuring that the treated wastewater is subjected to multiple passes past the UV bulb, thereby assuring greater irradiation and a more efficient killing of bacteria and microbes than would be accomplished by a single pass through the housing containing the UV light assembly.

Referring now to FIG. 6, there is shown another embodiment of the disinfecting system of the present invention. The embodiment shown in FIG. 6 is similar to that shown in FIG. 3 with the exception that rather than the air lift system used in FIG. 3 to pump water up the second flow path 62, in the embodiment of FIG. 6 a submersible pump 120 is used to pump treated wastewater W into inlet 32 where it passes through UV disinfectant apparatus 28A, back through outlet 34 into vessel 12A holding treated wastewater W.

Referring now to FIG. 8 there is shown another embodiment of the UV disinfecting system of the present invention. The embodiment shown in FIG. 8 is very similar to that shown in FIG. 6 with the exception that UV disinfecting unit 28B has an inlet 122 through the bottom wall 124 of housing 30B. In the embodiment shown in FIG. 8, there are no partitions dividing UV unit 28B into first and second flow pathways. Rather, UV unit 28B is comprised of a UV bulb 126 encased in a coarse or other UV transparent sheath 128 such that water flowing upwardly through housing 30B under the influence of submersible pump 120 essentially surrounds the bulb assembly 126 and flows outwardly through outlet 34 back into treated wastewater W in vessel 12A. However, once again the treated wastewater W is being continuously recirculated past UV bulb assembly 128 so long as pump 120 is running.

Referring now to FIG. 10 there is shown another embodiment of the present invention for ensuring that treated wastewater W is exposed to multiple passes past the UV bulb. The embodiment of FIG. 10, shown generally as 130 comprises a tank or vessel 132 having an inlet 134 and an outlet 136. Vessel 132 is provided with a neck 138 extending out of the top of vessel 132, neck 138 being covered by a removable cover 140 thereby forming an access hatch for maintenance on the interior of vessel 132. While in the embodiments discussed above, the UV bulb has been oriented in a generally vertical disposition, in the embodiment shown in FIG. 10 the UV bulb is mounted generally horizontally. To this end, brackets, 142 and 144 suspended in a suitable manner from the lower end of neck portion 138 support a housing shown generally as 146 comprised of a removable cover 148 in which is disposed a UV bulb assembly 150 comprised of an elongate UV bulb and a suitable quartz sheath. UV bulb assembly 150 is suspended from cover 148 of housing 146 by a pair of hanger brackets 152 and 154. UV bulb assembly 150 extends between sockets 156 and 158 and is connected to an electrical power source via line 160 extending through a conduit 162 which in turn extends to cover 140 and into electrical component box 164. To disinfectant treated wastewater W, a submersible pump 168 pumps treated wastewater W from vessel 132 through conduit 170 into the interior of housing 146 to a level above UV bulb assembly 150. An overflow pipe 172 extending through a bottom wall of housing 146 allows UV treated wastewater in housing 146 to pass back into vessel 132. Accordingly, treated wastewater W can be continuously recycled past UV bulb assembly 150, so long as pump 168 is running.

Referring now to FIG. 11 there is shown yet another embodiment of the present invention for recycling treated wastewater past the UV disinfecting bulb assembly. The embodiment of FIG. 11 is shown generally as 180 for running treated wastewater W. Vessel 182 has a neck 184 and a cover 186. Brackets 188 and 190 extend from the lower end of neck 184 and serve to hold a housing shown generally as 192. Housing 192 is connected to an angled chute 194 which in turn is connected to an outlet 196 which in turn is connected to a conduit 198 extending through cover 186 and being in open communication with electronics box 200. A UV bulb assembly shown generally 202 comprising a UV bulb 204 and a quartz or similar UV transparent sheath 206 is connected to a flex connection 208 which in turn is connected to tubing 210, electrical wires 212 extending through tubing 210 and connecting bulb 204 with electronics box 200. A submersible pump 220 pumps treated wastewater through a standpipe 222 to an outlet 224 such that treated wastewater W flows into housing 192.

An overflow pipe 226 conveys irradiated, treated wastewater out of housing 192 back into vessel 182 where, via the action of pump 220 it is recycled past the UV bulb assembly 202. Additionally, since UV bulb assembly is essentially continuously immersed in the treated wastewater in housing 192, it receives a higher dose of radiation and therefore a higher kill rate of microorganisms and bacteria. It will be understood that rather than the overflow pipe 226, the treated wastewater could be pumped through housing 192 at a sufficient rate such that the bulb assembly 202 would be substantially immersed while pump 220 is running.

Figure 12:
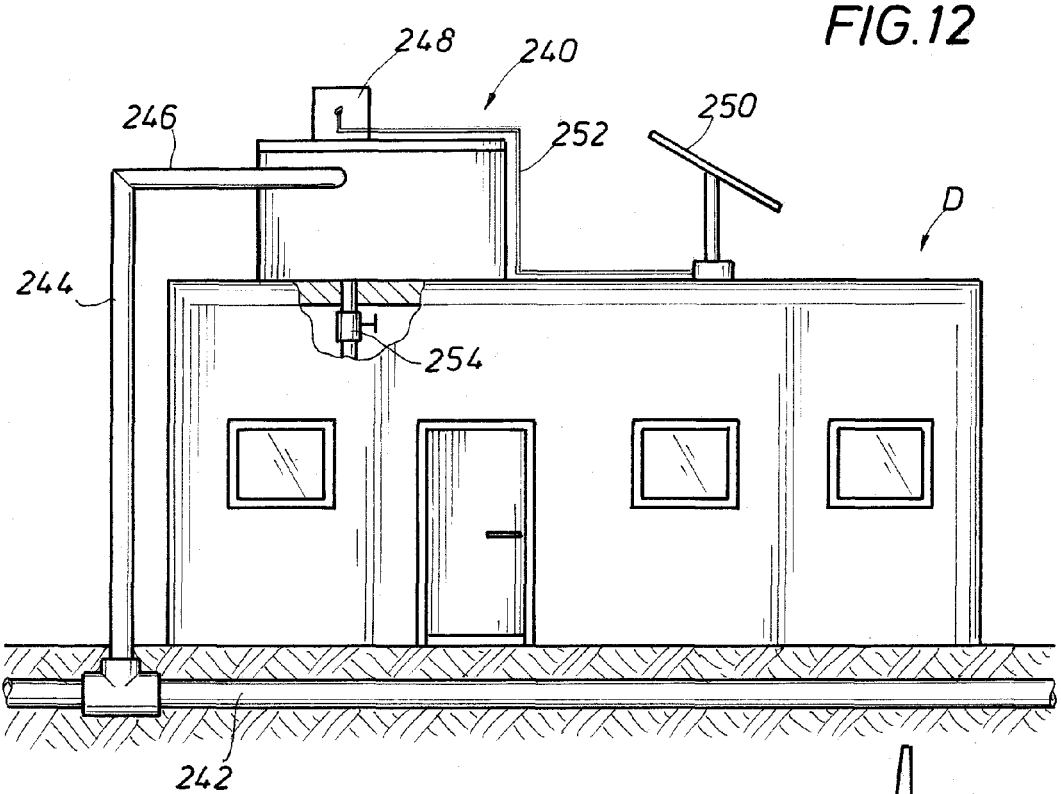
FIG. 12 is an elevational view showing the disinfectant system of the present invention in conjunction with a solar panel to supply alternative energy to the electrical components of the UV disinfectant system.
Figure 13:
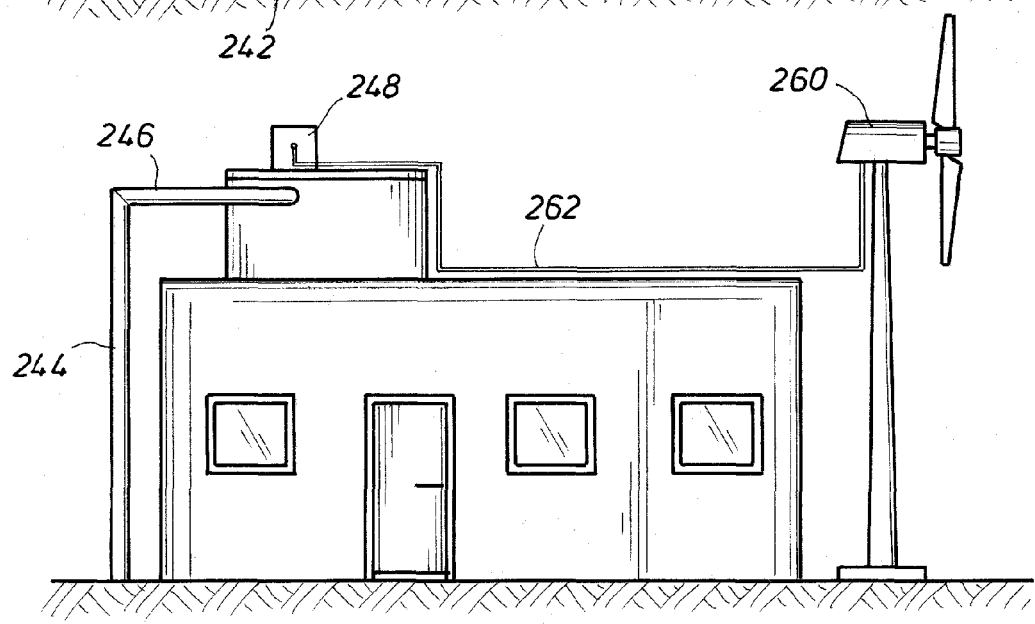
FIG. 13 is a view similar to FIG. 12 showing the UV disinfectant system of the present invention in conjunction with a wind power turbine.

Referring now to FIGS. 12 and 13 there is shown another embodiment of the UV disinfectant system of the present invention employing the use of alternative energy for electric power. Referring first to FIG. 12, there is shown a dwelling D, which could be a residence, business, etc., but which, in any event, is suitable for human habitation. Mounted on the roof of dwelling D is a UV disinfection system 40 of one of the types described above. UV disinfection system 240 comprises a holding tank (not shown) into which water from a water main 242 is transferred via a riser 244 and an inlet pipe 246. An electronic component box 248 which operates a UV bulb assembly and any pump systems such as of the various types described above is connected to a solar panel array 250 by power lines 252. The outlet from the holding vessel or tank from system 240 is connected to a main valve 254 which, when in the open position, allows water to flow into dwelling D for use in showers, faucets, etc. which are accessible by users in dwelling D. Since all the electric power needs for UV disinfectant system 240 are furnished by solar panel arrays 250, the alternative energy system is particularly desirable for use in underdeveloped, particularly rural, areas where contaminated water may be present in main line 242. In particular, one of the UV disinfectant systems described above wherein water is recycled past the UV bulb assembly, whatever its configuration, it is particularly desirable for use since it ensures a greater level of decontamination. Furthermore, since there is a recycle of contaminated water past the UV bulb whenever the pump or any pump system is operating to move water past the UV bulb, a smaller UV bulb can be employed needing less power consumption. However, the effectiveness of the UV irradiation is enhanced because of multiple passes of the contaminated water past the UV bulb.

Turning to FIG. 13 it is shown another embodiment of the alternative energy system of the present invention wherein the source of alternative energy is wind turbine 260 which supplies power via power line 262 to electronic component box 248.

Although specific embodiments of the invention have been described herein in some detail, this has been done solely for the purposes of explaining the various aspects of the invention, and is not intended to limit the scope of the invention of the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A system for disinfecting contaminated water comprising:
   a vessel for contaminated water and having a vessel inlet and a vessel outlet;
   an elongate housing disposed generally vertically in said vessel, said housing having a housing inlet, a housing outlet and a bottom wall, said housing outlet being in open communication with the interior of said vessel;
   an elongate, UV light assembly generally vertically disposed in said housing, said light assembly comprising a pair of vertically extending first and second partitions and an elongate UV bulb disposed between said first and second partitions, said first and second partitions and said UV bulb serving to divide said housing into a first portion in open communication with said housing inlet and a second portion in open communication with said housing outlet, said first portion defining a first vertically oriented first flow pathway, said second portion defining a second vertically oriented second flow pathway, said first flow pathway and said second flow pathway being opposite in direction to each other and both said first and second flow pathway are exposed to radiation from said elongate UV bulb, said first flow pathway being in open communication with said housing inlet for flow of contaminated water from said vessel and said second flow pathway being in open communication with said housing outlet and said first flow pathway for flow of water out of said housing and into said vessel; and
   a flow inducer aiding flow of at least some of said contaminated water from said vessel through said housing and out said housing outlet.

2. The system of claim 1, wherein said housing inlet and said vessel inlet are connected by a conduit, said conduit having an opening through which contaminated water in said vessel can pass into said housing under the action of said flow inducer.

3. The system of claim 2, wherein said conduit comprises a T-fitting having first and second legs, said first and second legs being generally horizontally disposed in said vessel, one end of said first leg of said T-fitting being connected to said vessel inlet, the other end of said first leg of said T-fitting being connected to said housing inlet, said second leg of said T-fitting having an opening in open communication with the interior of said vessel.

4. The system of claim 3, wherein there is a flow restrictor in said second leg of said T-fitting.

5. The system of claim 4, wherein said flow restrictor comprises a weir.

6. The system of claim 2, wherein said flow inducer comprises a gas source disposed below said opening, said gas source producing an upwardly flowing gas stream which lifts contaminated water in said vessel below said opening sufficient to aid said flow of contaminated water through said housing.

7. The system of claim 1, wherein said flow inducer comprises a gas source disposed in said housing below said second flow pathway and forming an upwardly flowing gas stream.

8. The system of claim 1, wherein said housing inlet and said vessel inlet are connected by a conduit, said conduit having an upwardly facing opening and said inducer comprises a gas lift assembly for moving contaminated water from said vessel into said opening of said conduit.

9. The system of claim 8, wherein said gas lift assembly comprises an elongate, generally vertically disposed tube having an upper portion in open communication with said opening and a lower open end in open communication with contaminated water in said vessel and a source of gas disposed below said lower open end of said tube whereby contaminated water in said vessel is moved up said tube into said opening.

10. The system of claim 1, wherein said vessel outlet is connected to a pump disposed in said vessel for pumping contaminated water out of said vessel outlet.

11. The system of claim 1, wherein contaminated water in said vessel flows out of said vessel by gravity.

12. The system of claim 1, wherein said UV bulb is exposed to contaminated water in both said first and second flow pathways.

13. The system of claim 1, wherein said UV light assembly is spaced from said bottom wall of said housing.

14. The system of claim 1, wherein said flow inducer is a pump system.

15. The system of claim 14, wherein said pump system comprises a submersible pump.

16. An alternative energy system for disinfecting contaminated wastewater comprising:
   the system of claim 1; and
   an alternative energy source positionable in the vicinity of said alternative energy system for applying electric power to at least one of said UV bulb and said flow inducer.

17. The alternative energy system of claim 16, wherein said UV disinfectant system is positioned at an elevated position relative to a user accessible outlet below said elevated position.

18. The alternative energy system of claim 16, wherein said alternative energy source is one of solar energy or wind energy.

\* \* \* \* \*